United States Patent [19]

Ng

[11] Patent Number: 4,691,067

[45] Date of Patent: Sep. 1, 1987

[54] CATALYTIC PROCESS FOR COUPLING TELOMERS OF CHLOROTRIFLUOROETHYLENE

[75] Inventor: Johny S. Ng, Grand Island, N.Y.

[73] Assignee: Occidental Chemical Corporation, Niagara Falls, N.Y.

[21] Appl. No.: 502,884

[22] Filed: Jun. 9, 1983

[51] Int. Cl.$^4$ .............................................. C07C 17/26
[52] U.S. Cl. .................................... 570/153; 570/171; 570/175
[58] Field of Search ................ 570/153, 171, 175, 161

[56] References Cited

U.S. PATENT DOCUMENTS

| | | | |
|---|---|---|---|
| 2,587,599 | 3/1952 | Corson et al. ........................ | 502/329 |
| 2,705,229 | 3/1955 | Ruh et al. ............................ | 570/138 |
| 2,742,510 | 8/1956 | Davis ................................ | 570/156 |
| 2,802,887 | 8/1957 | Miller et al. ........................ | 570/156 |
| 2,875,253 | 2/1959 | Barnhart ............................ | 570/125 |
| 3,046,304 | 7/1962 | Haszeldine ......................... | 570/171 |
| 3,099,695 | 7/1963 | Muray ............................... | 570/161 |
| 3,505,417 | 4/1970 | Gardner ............................ | 570/156 |
| 3,876,557 | 4/1975 | Bland ................................ | 502/329 |
| 4,307,259 | 12/1981 | Dittman ............................. | 570/171 |

FOREIGN PATENT DOCUMENTS

| | | | |
|---|---|---|---|
| 538360 | 3/1957 | Canada ............................... | 570/257 |
| 761053 | 11/1956 | United Kingdom ............... | 570/161 |
| 774103 | 5/1957 | United Kingdom ............... | 570/172 |

*Primary Examiner*—Donald B. Moyer
*Assistant Examiner*—Joseph A. Boska
*Attorney, Agent, or Firm*—James F. Tao; William G. Gosz

[57] ABSTRACT

A process for coupling two low molecular weight telomers of chlorotrifluoroethylene comprises reacting the telomers with hydrogen in the presence of an effective amount of a catalyst to form a coupled olefin. The catalyst comprises palladium, platinum, rhodium, ruthenium, Raney nickel, Raney cobalt, and mixtures thereof, either supported or unsupported. The olefin can be fluorinated using a suitable fluorinating agent, such as chlorine trifluoride, to form a saturated telomer.

12 Claims, No Drawings

CATALYTIC PROCESS FOR COUPLING TELOMERS OF CHLOROTRIFLUOROETHYLENE

BACKGROUND OF THE INVENTION

The present invention relates to a process for coupling low molecular weight telomers of chlorotrifluoroethylene, hereinafter designated as "CTFE", to produce commercially useful products.

CTFE telomers are saturated, low molecular weight polymers, typically of general formula $CCl_3(CF_2CClF)_nCl$, where n, the molecular number or chain length (the number of repeating units in the telomer chain) is in the range of 1 to 20.

Various methods of preparing such CTFE telomers are known in the prior art and have been practiced commercially for many years. An article by William T. Miller, Jr. et al in *Industrial and Engineering Chemistry*, pages 333–337 (1947), entitled "Low Polymers of Chlorotrifluoroethylene", describes a process for producing low molecular weight polymers of CTFE by carrying out the polymerization in a solution of chloroform using benzoyl peroxides as a polymerization promoter. Other solvents disclosed in the reference as being useful for this purpose include carbon tetrachloride and tetrachloroethylene. The solution is heated in a pressure vessel for $1\frac{3}{4}$ hours at 100° C., and the unreacted CTFE monomer and chloroform are removed by distillation, leaving a "crude" telomer of general formula $CHCl_2(CF_2CClF)_nCl$, which can be further heated and distilled to yield products ranging from a light oil to a semi-solid wax or grease.

Another process which has been developed for producing low molecular weight CTFE polymers is described in U.S. Pat. No. 2,788,375, issued Apr. 9, 1957. This process comprises reacting CTFE with a saturated organic bromo compound, such as bromotrichloromethane, in the presence of actinic light in a deoxygenated system to obtain saturated bromopolychlorofluoro compounds containing one or more CTFE units per molecule. These saturated bromopolychlorofluoro compounds can then be converted to corresponding polychlorofluoro compounds by reaction with chlorine, and subsequently reacted with fluorinating agents to yield more highly fluorinated products.

A more recent development in this field is described in a series of articles by Y. Peitrasanta et al entitled "Telomerization by Redox Catalysis" appearing in the *European Polymer Journal*, Vol. 12 (1976). This technology involves the reaction of a chlorinated telogen, such as carbon tetrachloride, with CTFE in the presence of benzoin and a suitable redox catalyst, such as ferric chloride hexahydrate ($FeCl_3 \cdot 6H_2O$). The telomerization reaction is suitably carried out in acetonitrile which is a common solvent for the reactants and catalysts. The telomerization reaction can be illustrated as follows:

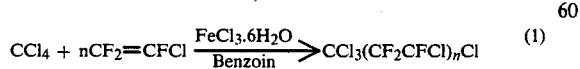

$$CCl_4 + nCF_2=CFCl \xrightarrow[\text{Benzoin}]{FeCl_3 \cdot 6H_2O} CCl_3(CF_2CFCl)_nCl \quad (1)$$

Such telomers can be fluorinated with known fluorinating agents, such as cobalt trifluoride, chlorine trifluoride or hydrogen fluoride to produce products which have a higher degree of stability, and are therefore of more commercial importance. Such fluorination processes are disclosed in British Patent Nos. 712,184 and 761,053, U.S. Pat. Nos. 2,636,908, and 2,886,607.

There are certain disadvantages inherent in all the methods used to produce CTFE telomers which are suitable for particular applications. For example, the production of hydraulic fluids or light oils typically requires telomers having a chain length of from 3 to 6 carbon atoms, while the production of greases or waxes requires longer chain length telomers, i.e. those having 12 or more carbon atoms in the chain. For such applications, it is desirable to maximize the yield of products having the specific characteristics as defined by the end user's product specifications. This necessitates a fairly narrow range of molecular weights in most instances. However, commercial processes actually produce a distribution of telomers having a comparatively wide range of molecular weights, including low molecular weight telomers, i.e. those having molecular numbers of 1 and 2, which due to their volatility have no commercial value.

In U.S. Pat. No. 4,307,259, a process is described for coupling trimers which are prepared by the gas phase photochlorination of bromotrifluoroethylene. The trimers, which are obtained by fractional distillation of the polymerization products, contain a single bromine atom on a single end group of each trimer. The trimers are reacted with one mole of zinc per two moles of trimer in the presence of acetic anhydride forming $ZnBr_2$, and a coupled, fully saturated product having twelve carbon atoms.

It is therefore a principle object of this invention to provide a process for coupling low molecular weight telomers of CTFE to produce unsaturated compositions of a higher molecular weight which can be further fluorinated to yield a stabilized product. It is further the object of this invention to provide a process for utilizing the lighter weight telomers from a CTFE telomerization process to produce higher molecular weight telomers useful as hydraulic fluids.

SUMMARY OF THE INVENTION

In accordance with the present invention, there is provided a process for coupling two low molecular weight telomers of chlorotrifluoroethylene comprising reacting said telomers with hydrogen in the presence of an effective amount of catalyst to from a coupled olefin. The catalyst system comprises platinum, palladium, rhodium, ruthenium, Raney nickel, Raney cobalt, and mixtures thereof. The catalysts can be present in elemental form or as compounds thereof, and can be unsupported or on a suitable support such as carbon or calcium carbonate.

The olefin prepared by this process can then be fluorinated to form a stabilized, saturated telomer useful as a nonflammable hydraulic fluid. Suitable fluorinating agents include chlorine trifluoride, cobalt trifluoride, and elemental fluorine.

DESCRIPTION OF THE PREFERRED EMBODIMENTS

The coupling process of the present invention comprises the reaction of two low molecular weight telomers of chlorotrifluoroethylene with hydrogen in the presence of an effective amount of a suitable catalyst. Such telomers can be initially prepared using a variety of techniques, although due to overall efficiency and convenience, it is preferred to prepare such telomers by reacting carbon tetrachloride with chlorotrifluoroethylene in an acetonitrile solvent in the presence of a catalytic amount of FeCl$_3$. This reaction can be illustrated as follows:

$$CCl_4 + nCF_2\!=\!CFCl \xrightarrow[M]{FeCl_3} CCl_3(CF_2CFCl)_nCl \quad (2)$$

wherein M is a metal or alloy selected from the group consisting of iron, nickel, cobalt, vanadium, molybdenum, chromium, their alloys and mixtures thereof. This process is conducted at a temperature in the range of from about 90° C. to about 150° C. and a pressure in the range of from about 150 p.s.i. to about 300 p.s.i., and is described in more detail in co-pending U.S. application Ser. No. 374,561, filed May 3, 1982.

In reaction (2), n designates the chain length of the telomer and will typically range from 1 to 20. However, the distribution of telomers within this range is nonuniform, with the lighter weight telomers generally comprising a disproportionately high percentage of the final product. As an example, a product distribution having from 20% to 30% of CCl$_3$(CF$_2$CFCl)Cl (wherein n=1), and 10% to 20% of CCl$_3$(CF$_2$CFCl)$_2$Cl (wherein n=2), is not unusual. Unfortunately, such lighter weight telomers are too volatile to be useful for most practical applications, such as nonflammable hydraulic fluids.

According to the present invention, however, such telomers can be coupled to form heavier and more useful products by reaction with hydrogen in the presence of a suitable catalyst. The following reaction illustrates the reductive catalytic coupling of two telomers having a chain length of 1 (n=1):

$$2Cl_3CCF_2CFCl_2 + 2H_2 \xrightarrow{Catalyst} \quad (3)$$
$$Cl_2FCF_2CClC\!=\!CClCF_2CFCl_2 + 4HCl$$

Reaction (3) can be suitably carried out at a temperature in the range of from about 100° C. to about 200° C., preferably in the range of from about 120° C. to about 160° C., and at a pressure in the range of from about atmospheric pressure to about 60 p.s.i.

The catalysts which are suitable for the process of this invention include the following metals: palladium, platinum, rhodium, ruthenium, Raney nickel, Raney cobalt, and mixtures thereof. These metals can be present in elemental form or as compounds thereof, either unsupported or on a suitable support. Typical catalyst supports include, for example, carbon, calcium carbonate, activated carbon, silicon carbide, silica gel, alumina, zirconia, titania, silica, kieselguhr, barium carbonate, pumice, zeolites, and the like. Suitable catalytic compounds include the following: palladium acetate, palladium chloride, platinum dioxide, and ruthenium dioxide. Accordingly, any reference to the aforementioned catalytic metals in this specification and appended claims is meant to include the corresponding catalytic compounds as well.

The amount of catalyst required in this process is in general dependent on the type of catalyst used and the reaction conditions. Amounts of catalyst in the range of from less than about 0.5% to about 5% or more by weight are generally suitable. When the catalysts are supported, it is generally preferred to use about 5% by weight of catalyst on the support substrate.

The reaction can be suitably carried our by bubbling a molar excess (an approximately 8 fold excess is desirable) of hydrogen gas into a telomer mixture in the presence of an effective amount of a catalyst, such as 1% by weight of 5% palladium on carbon, at about 140° C. over a period of 8 to 10 hours. The by-product HCl gas is removed and scrubbed with water, enabling more hydrogen to be dissolved for reaction. The product olefins can then be filtered off, leaving the catalyst behind.

The advantages of the catalytic process of the present invention over current or proposed processes are as follows:

1. The only significant by-product of the reaction is hydrogen chloride gas which can be conveniently converted to hydrochloric acid by scrubbing with water. This avoids many problems attendant with the use of a precipitating agent, such as product separation and purification.

2. Waste disposal and environmental problems are largely avoided.

3. No solvent is required, thus avoiding problems of product work-up and solvent distillation or extraction.

Reaction (3) proceeds in an unexpected manner in view of conventional processes directed to the reaction of an alkyl halide with hydrogen under typical hydrogenation conditions. For such processes, hydrogenolysis of the C-Cl bonds would normally be the predominant reaction as shown below:

$$R\!-\!X + H_2 \xrightarrow{Pd/C} R\!-\!H + HX \quad (4)$$

wherein R is an alkyl group, and X is chlorine, iodine or bromine.

In accordance with reaction (4) therefore, one would normally expect the reaction product HCl$_2$CCF$_2$CFCl$_2$ to predominate from reacting Cl$_3$CCF$_2$CFCl$_2$ and H$_2$ as shown in reaction (3).

In actual practice, very little (i.e. less than 3%), if any, of this product is actually obtained. Instead, the telomer is in effect dechlorinated to form an olefin. While not wishing to be bound to any theory of operability, it is speculated that the production of the olefin is due, in part, to the high reactivity of the telomer. However, if a high concentration of catalyst is used, i.e. more than about 10% by weight, than the hydrogenation products will appear and even predominate. Therefore, it is important to avoid this condition in the practice of this invention.

The olefins produced according to reaction (3) can be fluorinated to form a saturated, stabilized product. A suitable fluorinating agent for this purpose is chlorine trifluoride (ClF$_3$), although other fluorinating agents can be used. Cobalt trifluoride or ferric chloride can also be used as catalysts in combination with chlorine trifluoride. The addition of such cobalt or iron salts produces a product having slightly different characteristics and structure than the use of chlorine trifluoride alone. Such fluorination can be advantageously carried out at a temperature in the range of from about 80° C. to about 200° C.

Although the coupling reaction (3) has been described in terms of the reaction of two telomers of equivalent chain lengths, i.e. a chain length of 1, to produce an olefin of formula C$_6$F$_6$Cl$_6$, it should be appreciated that the process of this invention is applicable to any combination of low molecular weight CTFE telomers. Accordingly, the term "low molecular weight telomer", as used in the present specification and claims, is intended to denote a CTFE telomer of general formula $CCl_3(CF_2CClF)_nCl$, wherein n is in the range of 1 to 12.

The following examples are intended to further illustrate the various embodiments and advantages of the present invention without limiting it thereby. These examples illustrate the catalytic coupling of low molecular weight CTFE telomers to produce a coupled olefin which can then be reacted with a suitable fluorinating agent to produce a saturated product of higher molecular weight than either of the individual coupled telomers. Specifically, Example 1 illustrates the catalytic coupling of two telomers having a chain length of 1. Example 2 illustrates the catalytic coupling of two telomers having chain lengths of 1 and 2, while Example 3 illustrates the catalytic coupling of two telomers having a chain length of 2.

EXAMPLE 1

A 25 ml. round-bottom flask was equipped with a gas inlet, a water condenser and a thermometer. 27 Grams of $Cl_3CCF_2CFCl_2$ and 0.28 grams of a catalyst comprising 5% palladium on a carbon support were charged into the flask. The mixture was purged with nitrogen for five minutes and then warmed up to 140° C. Hydrogen gas was then bubbled in at 35ml/min for 9.3 hours. The by-product hydrogen chloride gas was absorbed in a water scrubber as an offgas.

After the reaction, the mixture was cooled to room temperature and filtered through a medium glass frit coated with a thin layer of alumina. G.C. and G.C./M.S. analyses indicated all the telomers had been converted into two isomers of the following coupled olefin:

$$Cl_2FCF_2CClC=CClCF_2CFCl_2$$

EXAMPLE 2

A 25 ml. round-bottom flask was equipped with a gas sparger, a water condenser and a thermometer. 13.5 Grams of $Cl_3CCF_2CFCl_2$, 19 grams of $Cl_3C(CF_2CFCl)_2Cl$, and 0.32 grams of 5% palladium on a carbon support were charged into the flask. The mixture was purged with nitrogen for five minutes and then warmed up to 140° C. Hydrogen gas was then bubbled in at 35 ml/min for 10 hours. The byproduct hydrogen chloride gas was absorbed in a water scrubber as an off gas.

After the reaction, the mixture was cooled to room temperature and filtered through a medium glass frit coated with a thin layer of alumina. G.C. and G.C./M.S. analyses indicated all the telomers have been coupled to provide a mixture of the following olefins:

$$Cl_2FCF_2CClC=CClCF_2CFCl_2$$

$$Cl_2FCF_2CClC=CCl(CF_2CFCl)_2Cl$$

$$Cl(CFClCF_2)_2ClC=CCl(CF_2CFCl)_2Cl$$

EXAMPLE 3

A 50 ml. round-bottom flask was equipped with a gas sparger, a water condenser and a thermometer. 10.3 Grams of $Cl_3C(CF_2CFCl)_2Cl$, and 0.05 grams of 5% palladium on a carbon support were charged into the flask. The mixture was purged with nitrogen for five minutes and then warmed up to 140° C. Hydrogen gas was then bubbled in at 35 ml./min. for 10 hours. The by-product hydrogen chloride gas was absorbed in a water scrubber as an off-gas.

After the reaction, the mixture was cooled to room temperature and filtered through a medium glass frit coated with a thin layer of alumina. G.C. and G.C./M.S. analyses indicated that all of the telomer had been converted to the following coupled olefin:

$$Cl(CFClCF_2)_2ClC=CCl(CF_2CFCl)_2Cl$$

While various embodiments and exemplifications of this invention have been shown and described in the specification, modifications and variations thereof will be readily appreciated by those skilled in the art. It is to be understood, therefore, that the appended claims are intended to cover all such modifications and variations which are considered to be within the scope and spirit of the present invention.

What is claimed is:

1. A process for coupling two low molecular weight chlorotrifluoroethylene telomers, each telomer having the general formula $CCl_3(CF_2CFCl)_nCl$, where n is one or two, to form a perchlorofluoroolefin of higher molecular weight, said process consisting essentially of reacting said telomers with hydrogen in the presence of an effective amount of a catalyst selected from the group consisting of platinum, palladium, rhodium, ruthenium, Raney nickel, Raney cobalt, and mixtures thereof.

2. The process of claim 1 wherein the catalyst is supported.

3. The process of claim 2 wherein the catalyst is palladium on a carbon support.

4. The process of claim 2 wherein the catalyst is palladium on a support of calcium carbonate.

5. The process of claim 1 wherein the catalyst is platinum dioxide.

6. The process of claim 1 wherein the reaction is conducted at a temperature in the range of from about 120° C. to about 160° C., and a pressure of from about atmospheric to about 60 p.s.i.

7. The process of claim 1 wherein the catalyst is present in the range of from about 0.5% to about 5.0% by weight of telomer.

8. A process for preparing a stabilized, saturated chlorotrifluoroethylene product from a pair of low molecular weight chlorotrifluoroethylene telomers, each telomer having the general formula $CCl_3(CF_2CFCl)_nCl$, where n is one or two, said process consisting essentially of the steps of:

(a) reacting said low molecular weight telomers with hydrogen in the presence of an effective amount of a catalyst selected from the group consisting of platinum, palladium, rhodium, ruthenium, Raney nickel, Raney cobalt, and mixtures thereof, to form a coupled perchlorofluoroolefin of higher molecular weight, (b) reacting the olefin with a fluorinating agent to form a saturated product.

9. The process of claim 8 wherein the fluorinating agent is chlorine trifluoride.

10. The process of claim 8 wherein the fluorination reaction in step (b) is conducted at a temperature of from about 120° C. to about 200° C.

11. The process of claim 1 wherein the coupled perchlorofluoroolefin is selected from the group consisting of $Cl_2FCF_2CClC=CClCF_2CFCl_2$, $Cl_2FCF_2CClC=CCl(CF_2CFCl)_2Cl$, and $Cl(CFClCF_2)_2ClC=CCl(CF_2CFCl)_2Cl$, and mixtures thereof.

12. The process of claim 8 wherein the coupled perchlorofluoroolefin is selected from the group consisting of $Cl_2FCF_2CClC=CClCF_2CFCl_2$, $Cl_2FCF_2CClC=CCl(CF_2CFCl)_2Cl$ and $Cl(CFClCF_2)_2ClC=CCl(CF_2CFCl)_2Cl$, and mixtures thereof.

* * * * *